United States Patent
Ng (10) Patent No.: US 11,648,125 B2
(45) Date of Patent: May 16, 2023

(54) MODULAR MEGAPROSTHESIS HAVING A THREADED STEM AND METHODS THEREFOR

(71) Applicant: Vincent Ng, Reisterstown, MD (US)

(72) Inventor: Vincent Ng, Reisterstown, MD (US)

(*) Notice: Subject to any disclaimer, the term of this patent is extended or adjusted under 35 U.S.C. 154(b) by 147 days.

(21) Appl. No.: 16/212,965

(22) Filed: Dec. 7, 2018

(65) Prior Publication Data
US 2019/0175353 A1 Jun. 13, 2019

Related U.S. Application Data

(60) Provisional application No. 62/596,195, filed on Dec. 8, 2017.

(51) Int. Cl.
*A61F 2/38* (2006.01)
*A61F 2/30* (2006.01)

(52) U.S. Cl.
CPC ........ *A61F 2/3859* (2013.01); *A61F 2/30734* (2013.01); *A61F 2/3836* (2013.01); *A61F 2002/3085* (2013.01); *A61F 2002/30113* (2013.01); *A61F 2002/30224* (2013.01); *A61F 2002/30354* (2013.01); *A61F 2002/30395* (2013.01); *A61F 2002/30405* (2013.01); *A61F 2002/30433* (2013.01); *A61F 2002/30448* (2013.01); *A61F 2002/30449* (2013.01)

(58) Field of Classification Search
CPC ................. A61F 2/3662; A61F 2/3676; A61F 2002/368; A61F 2/3859; A61F 2/3836; A61F 2/30734; A61F 2002/30433; A61F 2002/30354; A61F 2002/30395; A61F 2002/3085; A61F 2002/30224; A61F 2002/30449; A61F 2002/30113; A61F 2002/30448; A61F 2002/30405
See application file for complete search history.

(56) References Cited

U.S. PATENT DOCUMENTS

| | | | | |
|---|---|---|---|---|
| 5,122,133 A | * | 6/1992 | Evans | A61B 17/742 606/300 |
| 5,961,555 A | * | 10/1999 | Huebner | A61F 2/40 623/19.11 |

(Continued)

OTHER PUBLICATIONS

Bousquet et al., (1984) "A Screw-Anchored Intramedullary Hip Prosthesis." In: Morscher E. (eds) The Cementless Fixation of Hip Endoprostheses. Springer, Berlin, Heidelberg, pp. 242-243; https://doi.org/10.1007/978-3-642-69006-8_38.

(Continued)

*Primary Examiner* — Brian A Dukert
*Assistant Examiner* — Melissa A Hoban
(74) *Attorney, Agent, or Firm* — Calderon Safran & Cole PC (57) ABSTRACT

The present invention relates to a prosthesis, such as a megaprosthesis, for a joint replacement or any segmental bone deficit. In particular, the present invention relates to a stem for a prosthesis having threads on at least part of an outer surface thereof. A prosthesis, such as a megaprothesis, is also provided. The prosthesis contains the threaded stem and a modular body engaged to the stem. The modular body contains a bone replace segment or a replacement joint, such as replacement knee joint, hip joint, shoulder joint, wrist joint, ankle joint, elbow joint, joints of the hand, joints of the foot, etc.

16 Claims, 6 Drawing Sheets

(56) References Cited

U.S. PATENT DOCUMENTS

| | | | | |
|---|---|---|---|---|
| 6,197,065 B1* | 3/2001 | Martin | ............... | A61B 17/164 |
| | | | | 623/23.17 |
| 7,156,879 B1* | 1/2007 | Albrektsson | .......... | A61F 2/3601 |
| | | | | 623/23.14 |
| 7,998,218 B1* | 8/2011 | Brown | ............... | A61F 2/3607 |
| | | | | 623/20.35 |
| 2002/0058999 A1* | 5/2002 | Dwyer | ............... | A61F 2/30734 |
| | | | | 623/22.42 |
| 2006/0129247 A1* | 6/2006 | Brown | ............... | A61F 2/3607 |
| | | | | 606/62 |
| 2014/0114362 A1* | 4/2014 | Giersch | ............... | A61B 17/864 |
| | | | | 606/304 |
| 2016/0030180 A1* | 2/2016 | Wecker | ............... | A61F 2/3609 |
| | | | | 623/18.11 |
| 2016/0206433 A1* | 7/2016 | Grostefon | ............ | A61F 2/3609 |

OTHER PUBLICATIONS

Pedtke et al. "Aseptic Failure: How Does the Compress® Implant Compare to Cemented Stems?", Clin Orthop Relat Res. Mar. 2012; V.470(3): pp. 735-742. Published online Nov. 2, 2011; doi: 10.1007/s11999-011-2159-5 https://www.ncbi.nlm.nih.gov/pmc/articles/PMC3270164/.
Integrum (2019), OPRA Implant System, Mölndal, Sweden, Available online: http://integrum.se/our-solutions/opra-implant-systems/ (accessed on Mar. 12, 2019).
Stryker SA (2008), GMRS Proximal Femoral Surgical Protocol brochure, Montreux, Switzerland, pp. 1-32 https://orto.hi.is/skrar/gmrsproximalfemurop-658.pdf.

* cited by examiner

MODULAR MEGAPROSTHESIS HAVING A THREADED STEM AND METHODS THEREFOR

CROSS-REFERENCE TO RELATED APPLICATIONS AND CLAIM TO PRIORITY

This application claims priority to U.S. Provisional Patent Application No. 62/596,195, filed Dec. 8, 2017, which is incorporated herein by reference.

FIELD OF THE INVENTION

The present invention relates to a prosthesis, such as a megaprosthesis, for a joint replacement or any segmental bone deficit. In particular, the present invention relates to a stem for a prosthesis having threads thereon.

BACKGROUND

Megaprostheses are a typical approach for reconstructing major bone deficits, such as following orthopaedic oncologic surgery or revision joint replacement surgery. Many bone deficits are caused by surgical removal for infection or tumor, or the product of multiple revised total hips/knees, fractures, etc. Megaprostheses are different than standard total hips or total knees because megaprostheses procedures generally include removing the entirety of a joint surface, epiphysis, metaphysis and sometimes a portion of the diaphysis, and replacing it with an endoprosthetic. There are approximately 7000-7500 megaprostheses per year in the USA, of which the majority involve either the proximal or distal femur.

Megaprostheses are typically modular in that the stem and the body of the prosthesis are separate components and can be quickly and easily linked together in various combinations according to a particular patient's anatomy, the amount of bone needing to be replaced, the amount of bone needing to be replaced, and the surgical situation. The stem is the portion of the prosthesis that attains fixation in the existing native bone. The body is the portion of the prosthesis that replaces the missing segments of bone. In addition to situations in which the megaprosthesis is used to replace either end of the bone and the joint surface, megaprosthetic constructs can also be used to replace some of the middle or shaft/diaphysis of the bone, if this is the portion that is removed and the ends of the native bone are still intact.

Typical stems can be either cemented or uncemented in the native bone canal. The canal is the hollow inside of the bone where the soft bone marrow typically resides. For cemented stems, the stem is slightly undersized relative to the inside of the bone and a layer of cement is used to create a hold on the stem. The stability achieved using cement during surgery will not improve over time and the stem can loosen if the cement fails either in its bond to the stem or to the native bone. For uncemented stems, the stem is held inside the bone most often using a press-fit design. In this design, the stem is typically the same or slightly larger than the inside of the prepared native bone canal and it is impacted carefully into the canal. Prior to insertion of the stem by impaction with a mallet, the native bone canal is usually reamed to a diameter slightly smaller than the intended stem size to achieve a tight fit. This tight fit between the stem and the bone restricts relative movement of the stem in the early post-surgical period. The goal of the uncemented stem is that the native bone will eventually grow into or onto the stem (osteointegration) and provide long-lasting stability. The early stability of the stem to reduce relative micromotion is very important for successful osteointegration. If osteointegration of an uncemented stem does not occur, then the stem will eventually loosen and need to be revised.

To improve osteointegration, some stems use coatings such as hydroxyapatite and other modifications such as a roughened surface. To improve early stability, several other design features may also be used. In addition to improving osteointegration, a roughened surface can increase friction between the stem and the bone, providing a "scratch-fit" and reducing micromotion. The stem may be straight or bowed (e.g., bowed to match a patient's femur's slight bow; for example if the stem is sufficiently long). A straight stem in a straight canal is a construct that is inherently predisposed to loosening and the minimal stem length in most systems are at least 10-12 cm. Bowed stems may be less likely to rotate within the bony canal and reduce micromotion, but generally require even longer lengths of native bone to be available. For patients with bone defects, this amount of remaining bone is oftentimes not present. Stems may have longitudinal splines, such as near a distal tip, near a proximal collar, or all along the stem in order to engage the inside of the canal and to reduce rotational micromotion. The splines, however, do not prevent the stem from backing out. Some stems have holes to allow interlocking screws or cross-bolts to be placed perpendicularly through one side of the bone, through the stem, and through the other side of the bone to provide further stability.

Another type of uncemented megaprosthesis stem known as Compress provides compression between the collar of the implant and the end of the bone (i.e. at the junction of the collar of the implant and the bone) to increase the likelihood of osteointegration. Compression at the interface of bone and/or metal surfaces is known to improve osteointegration. The Compress allegedly also requires less length of native bone than traditional press-fit stems to gain stable fixation. However, Compress stems have a thin spindle that is generally mechanically insufficient to bear significant weight or stress without sufficient osteointegration. The Compress can be challenging to install accurately in order to achieve optimal results. Thus, Compress stems can have higher incidences of failure or mechanical issues in the early setting before osteointegration can occur.

Thus, typical megaprosthesis stems have multiple shortfalls. First, cemented stems often loosen over time despite good early stability. Cemented stems are best for elderly patients or patients without long survival prognoses. However, in patients with hard ("sclerotic") bone, there may not be significant porosity in the bone for cement to interdigitate with and cemented stems can loosen in the early period. Cemented stems require excellent technique to achieve an optimal cement mantle and it can be highly surgeon-dependent. Second, cemented or uncemented stems require relatively long segments of remaining native bone to achieve adequate fixation. The length of the shortest stems in most manufacturers' systems is at least 10-12 cm. Oftentimes, this length of bone is not available. Furthermore, if the stem needs to be revised in the future and the entire or majority of stem is cemented or osteointegrated, it can be very difficult to remove without sacrificing the entire length of bone which is attached to this length of stem. Small chisels must be used to break away the ingrown areas of bone or bonded cement and then a very large slap-hammer must be used to disimpact the stem. The bone is often broken in the process. Loss of bone for the length of the stem makes further operations much more difficult. Third, preparation of the bone canal for pressfit stems and sizing of the stem must be very precise and accurate to avoid either oversizing or undersizing the stem. This portion of the surgery is prone to misjudgment and inconsistency. Oversizing will result in fracture of the native bone during impaction which can be difficult to fix and will compromise fixation of the stem even after fixation. On the other hand, even slight undersizing will result in inadequate stability due to lack of scratch-fit between the bone and stem or due to plastic adaptation of the bone over time. If the stem is unstable, then osteointegration will not occur. Fourth, traditional pressfit stems, regardless of scratchfit or longitudinal splines, do not hold or preserve the compression forces of the stem collar against the native bone junction achieved during initial insertion of the stem with impaction. The lack of a tight interface between the stem collar and the bone junction inhibits osteointegration. Fifth, traditional pressfit or cemented stems that have ingrowth or are bonded to the bone along the entire length of the stem will lead to stress-shielding of the bone. This results in thinning, resorption or atrophy of the bone near the collar.

Up to 30% of cemented or uncemented megaprosthesis stems have been reported to fail over time due to loosening. Therefore, there exists a need for an improved stem design which reduces or eliminates failure.

SUMMARY OF THE INVENTION

It is therefore an aspect of the present invention to provide a threaded stem for a megaprosthesis for replacing a patient's bone deficit or joint. The stem contains a shaft having threads on at least part of an outer surface thereof.

Another aspect of the present invention provides a prosthesis, such as a megaprosthesis, containing the above described threaded stem and a modular body engaged to the stem. The modular body contains a bone replace segment or a replacement joint, such as replacement knee joint, hip joint, shoulder joint, wrist joint, ankle joint, elbow joint, joints of the hand, joints of the foot, etc.

The present invention provides many advantages compared to other types of fixation (e.g., impaction, splined, cement, etc.), including: 1) increased stability and fixation of the stem even when placed in relatively short segments of bone; 2) increased tolerance for stem sizing mismatch between the prepared bone and the stem to gain purchase in the native bone canal of the threads compared to the relatively small asperities of the roughened surface of typical scratch-fit stems; 3) increased degree of control in regards to the amount of force required for inserting the threaded stem compared to impaction of typical stems; 4) increased compression at the megaprosthesis-bone interface at or near the collar (e.g., by the threads of the stem pulling the stem into the bone) and maintenance of the compression by means of the crossing interlocking mechanism; 5) decreased likelihood of pull-out failure or backing out of the stem with longitudinal forces; 6) increased ease of removal of the stem in case of infection or complications; 7) preserved bone stock by limiting stress-shielding; and 8) reduced likelihood of mechanical breakage of the stem by not using a thin spindle as in the Compress device.

Other aspects of the invention, including apparatus, devices, method, and the like which constitute part of the invention, will become more apparent upon reading the following detailed description of the exemplary embodiments.

BRIEF DESCRIPTION OF THE DRAWINGS

The foregoing background and summary, as well as the following detailed description of the drawings, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE PREFERRED EMBODIMENTS

Referring to the drawings, where like reference numerals refer to like components, the present invention provides a threaded modular megaprosthesis 100 for replacing a patient's segmental bone deficit or joint, such as the femur, knee joint or hip joint. The threaded modular megaprosthesis 100 is configured to improve the ease of placing a megaprosthesis stem, and to reduce the likelihood of implant failure, such as by inadvertent bone fracture, aseptic loosening of the stem, and the like. Generally, megaprostheses are endoprostheses for reconstructing substantial skeletal defects. Furthermore, modular megaprostheses are endoprostheses that include many assembled components.

The megaprosthesis 100 of the present invention includes a modular body 110 and a stem 112. In use, the stem 112 is implanted into the bone canal of the patient. The modular body 110 contains an artificial joint that is coupled to the stem 112 by mechanical means, such as screw, nut/bolt, rivets, cement, male/female coupling, or combinations thereof. The modular body 110 may include an intercalary segment of bone or a replacement joint such, as knee joint, hip joint, shoulder joint, wrist joint, ankle joint, elbow joint, joints of the hand, or joints of the foot. Commercially available replacement joints or segments of bone reconstruction may be, but not limited to, Megasystem-C from Link Orthopeaedics, GMRS from Stryker, OSS from Biomet, or ZSS from Zimmer. The present invention may use modular bodies 110 provided by currently available megaprostheses. However, the stem 112 of the present invention provides a threaded mechanism for improved implant stability, ease of removal, and other aforementioned advantages.

Figure 1:
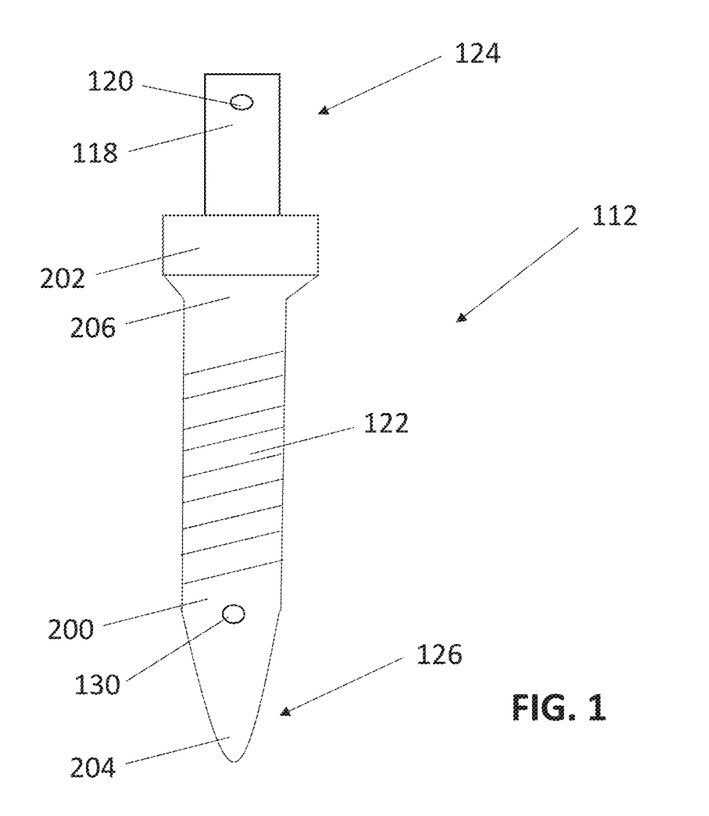
FIG. 1 is a drawing of a threaded stem according to the present invention.

FIG. 1 illustrates the stem 112 of the present invention. The stem 112 contains a proximal end 124 and distal end 126. Linearly, from the proximal end 124 to the distal end 126, the stem 112 preferably contains an intercalary segment 118, a collar 202, and a shaft 200. The collar 202 is intermediary to and connects the shaft 200 to the intercalary segment 118. The collar 202 connects to the shaft 200 on one side and to the intercalary segment 118 on the other opposing side. Preferably, the intercalary segment 118, collar 202, and shaft 200 are preferably linearly aligned and have a common central axis. Preferably, the stem 112 is a unitary body made of steel, titanium, cobalt chromium, tantalum, or combinations thereof. The stem 112 may be made using techniques known in the art, such as, but not limited to, forging, molding, machining, laser shaping, stereo lithography, sintering, or combinations thereof.

The shaft 200 is generally cylindrical and contains threads 122 over a portion thereof between the distal end 126 and the collar 202. The threads 122 is preferably located at a middle point between the distal end 126 and the collar 202 and cover at least 50%, more preferably 65%, most preferably 80%, of the surface of the shaft 200. In certain embodiments, the threads 122 completely cover the shaft 200. Preferably, the threads 122 is right handed such clockwise turn advance the shaft 200 (and the stem 112) into the bone. Preferably, the thread depth is about 1 to about 2.5 mm, but may vary depending on the size of the stem 112. The distal end 126 of the shaft 200 is preferably tapered to form a pointed end 204 to facilitate insertion of the stem 112 into the bone canal when in use. The portion 206 of the shaft adjacent to the collar 202 and between the threads 122 and the collar 202 is preferably tapered toward the outer diameter of the collar 202, such that the diameter of the portion 206 of the shaft adjacent to the collar 202 is larger than the diameter of the shaft in the location of the threads 122. The portion 206 also preferably contains a roughened, knurled, or porous surface, and/or a coating (e.g. hydroxylapatite) to provide a surface area for bone ingrowth. In the embodiment where the threads 122 completely cover the shaft 200, the threads adjacent to and near the collar may be roughed, knurled, and/or coated to encourage bone ingrowth. It is preferable that only portion 206 adjacent to the collar 202 or threads 122 adjacent to the collar 202 is roughened, knurled, porous, or coated, while other portions of the shaft are not. Bone in-growth is desired only near the collar 202 to prevent stress shielding.

The shaft 200 preferably contains an aperture 130 for fixing and holding the stem 112 in place when it is implanted into the bone. The central axis of the aperture 130 is preferably perpendicular to the central axis of the stem 112. The aperture 130 may be placed anywhere on the shaft 200; however, it is preferably placed between the threads 122 and the distal end 126. The aperture 130 may be a through hole or a blind hole, and in certain embodiments may be threaded. When the stem 112 is placed in the bone, a cross-pin 128 (see FIG. 2A) may be placed through the bone and into the aperture 130 to hold the stem 112 in place to prevent it from backing out of the bone on its threads 122. The cross-pin 128 may be, e.g., a screw, nut, retainer pin, bolt, or combinations thereof. Although one aperture 130 is illustrated in the drawings, it is understood that more than one apertures 130 may be formed in the shaft 200. The aperture 130 preferably has a diameter of about 3 to about 5 mm. In embodiments where more than one apertures 130 are present, it is preferable that the apertures 130 are perpendicular to the center axis of the shaft 200 and are at an angle to each other. Preferably, 2 to 4 apertures 130 are present along the length of the shaft 200. If two apertures 130 are present, it is preferably that the apertures 130 are about 90° to each other.

The collar 202 is intermediary to and connects the shaft 200 to the intercalary segment 118. The collar 202 may generally be cylindrical with a diameter greater than that of the shaft 200. In certain embodiments, the collar 202 may have a polygonal perimeter, such as hexagonal, pentagonal, or square, with flat sides configured to mate with a tool, e.g. a torque wrench, to screw and advance the stem 112 into the bone. For advancement of the stem 112 into the bone, the tool may engage the collar or the intercalary segment 118. Like the portion 206, the collar 202 may also be roughened, knurled, porous, or coated to encourage bone in-growth.

The intercalary segment 118 is formed on one side of the collar 202 and serves as an attachment for the modular body 110. Although the drawings depict the intercalary segment 118 as a cylindrical extension of the collar 202, the intercalary segment 118 may have varied shapes and configurations to accommodate mechanical attachment of the modular body 110. The connection between the modular body 110 and the intercalary segment 118 preferably allows for the modular body 110 to be rotated around the intercalary segment 118 for adjustments during surgery to proper orient and align of the joint. In certain embodiments, the modular body 110 may be formed directly on the intercalary segment 118 to provide a monoblock implant.

Figure 3:
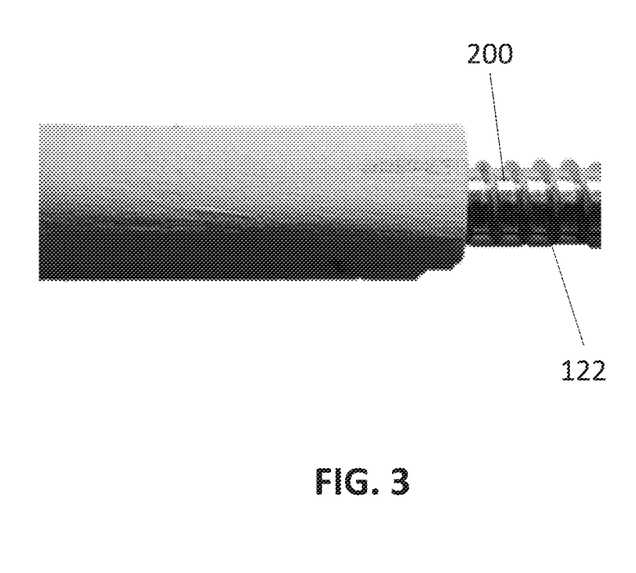
FIG. 3 is an image illustrating a side view of the threads of the threaded stem partially threaded into a bone.
Figure 4:
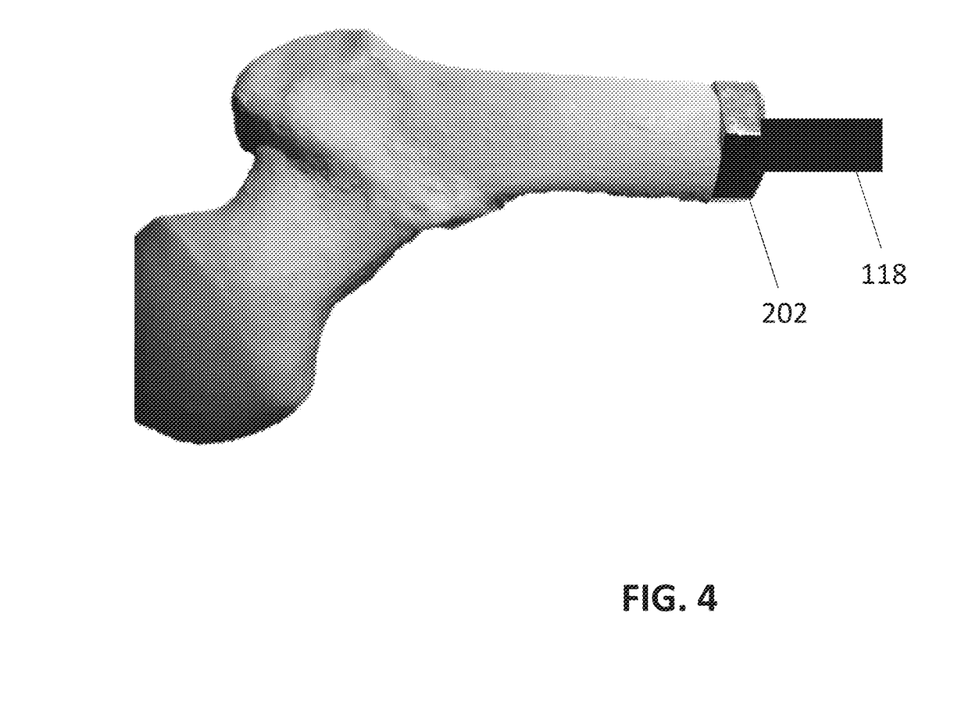
FIG. 4 is an image of another side view of the threaded stem fully inserted into a bone such that only the collar which has a tight interface with the native bone junction is showing.

When in use, the stem 112 is screwed into the bone (see FIG. 3), cemented or uncemented, until the collar 202 is flushed against the cut surface of the bone (see FIG. 4). Preferably, the stem 112 is overtightened so that the collar 202 compresses against the bone. The overtightening should be as firm as possible without stripping the threads through the bone or fracturing the bone. It is believed that the overtightening compresses the bone which encourages osteointegration with the stem 112. Once the stem 112 is in place, the cross-pin 128 may be placed through the bone and into the aperture 130 to fix and hold the stem 112 in place and to prevent it from backing out of the bone. The alignment of the aperture 130 and the cross-pin 128 may include techniques known in the art which may utilize a jig, x-ray, or fluoroscopy to locate the aperture 130 inside the bone. The modular body 110 may then be connected to the intercalary segment 118 or the fixed stem 112.

Figure 2:
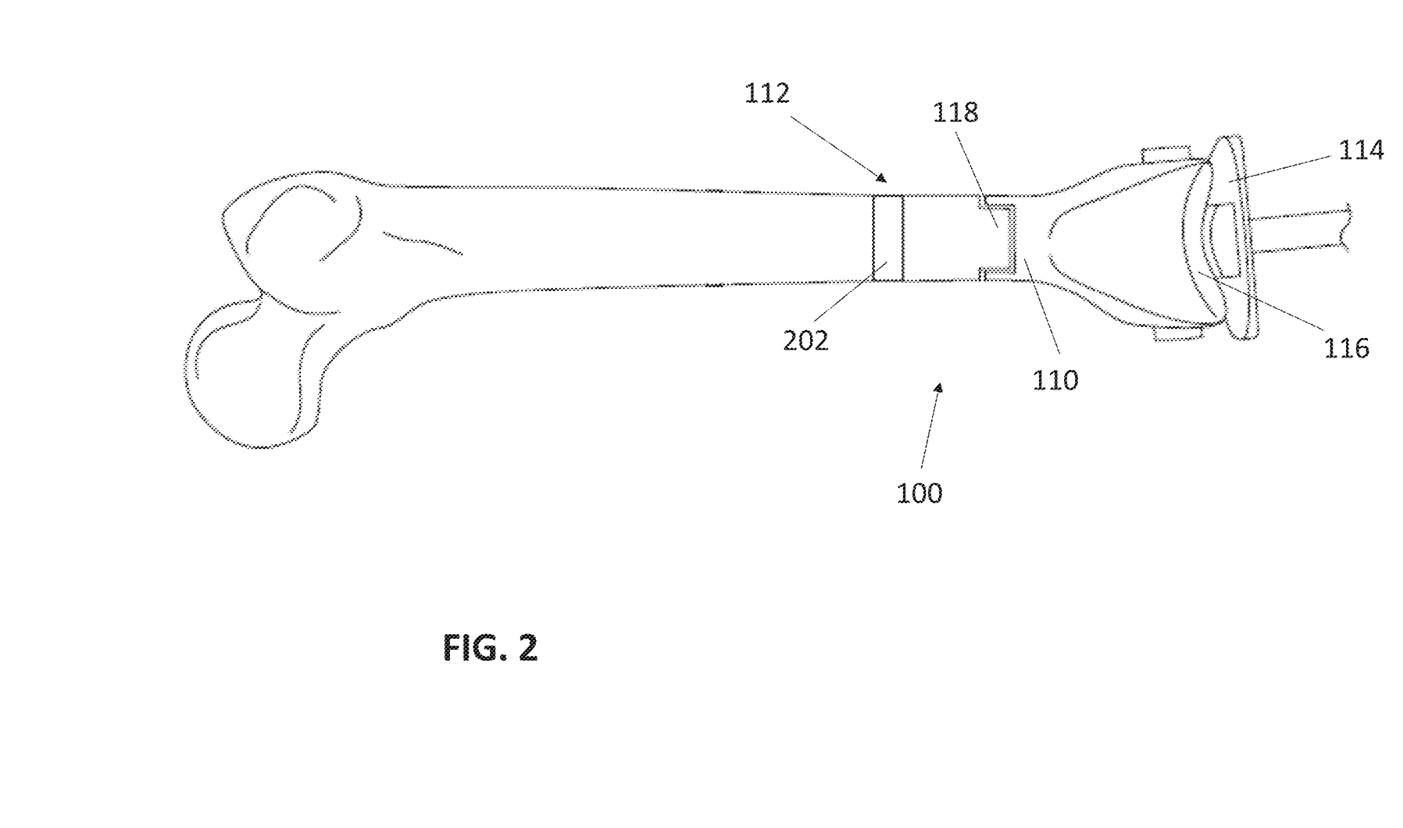
FIG. 2 is an illustration of a modular megaprosthesis for a knee revision, according to one embodiment of the present invention, threaded into a bone.
Figure 2A:
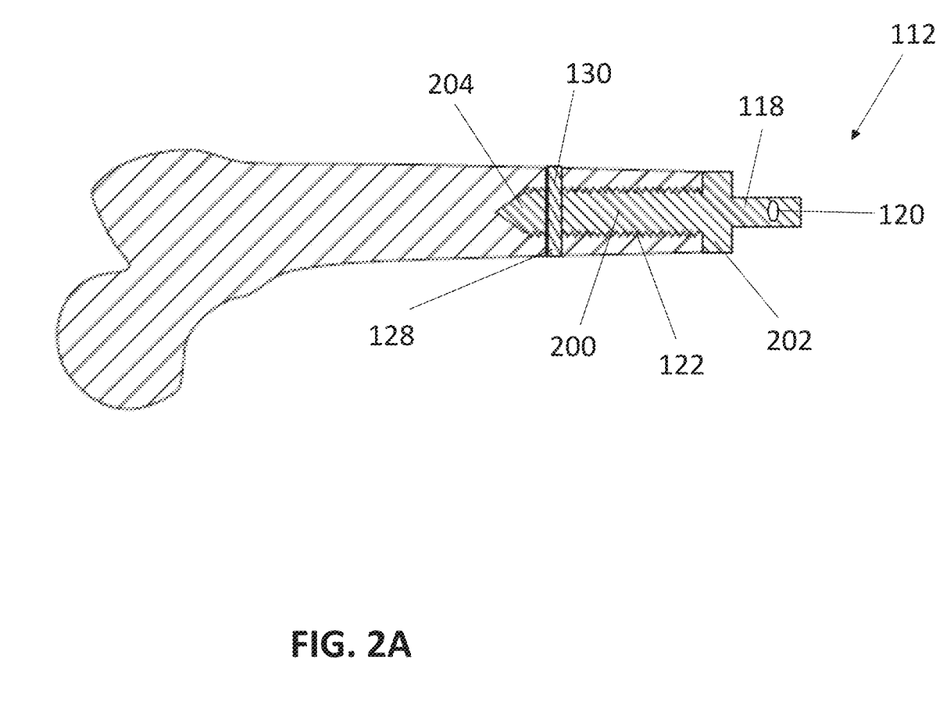
FIG. 2A is a schematic of the modular megaprosthesis for a knee revision of FIG. 2.

FIGS. 2 to 2A and the description below may refer to a knee joint replacement and a femur; however, the use of the stem 112 is the same regardless of the joint and/or bone being replaced. The modular body 110 may be a knee joint or any other joints or a segment to replace lost bone (e.g. to cancer), but the stem 112 remains the same.

In one embodiment, shown in FIGS. 2 and 2A, the megaprosthesis 100 includes a modular body 110, and a stem 112. The body 110 further includes a femoral attachment 114 to facilitate knee joint replacement (see FIG. 2). The femoral attachment 114 engages with an attachment 116 fixed to an opposing bone (e.g., the patient's tibia), such that the femoral attachment 114 pivots with respect to a plate through a finite arc to allow substantially normal knee movement. The femoral attachment 114 is coupled to the stem via an angular attachment or intercalary segment 118, as described below. The stem 112 is configured to be secured in the diaphysis portion of the femur (see FIGS. 2-5). Thus, the megaprosthesis 100 is configured to be fixed into the patient's bone according to many common methods that facilitate substantially normal knee movement. For example, the megaprosthesis 100 can be placed using methods for attaching prosthetics to bones that are considered high-weight-bearing, including impaction, cross-drilling, and the like, as further described below.

Still referring to FIGS. 2 and 2A, the modular body 110 is configured to couple to the stem 112 via the intercalary segment 118 (see FIG. 2). The modular body 110 is configured to be coupled to the intercalary segment 118 according to typical methods (e.g., fasteners), such as by bolting, screwing, pining, riveting, and the like. Furthermore, the intercalary segment 118 is configured to be coupled to the stem at various angles of rotational orientation with respect to a longitudinal axis of the femur. For example, the intercalary segment 118 may be coupled to the stem 112 wherein each component are aligned in an anterior direction. In another example, intercalary segment 118 may be coupled to the stem wherein one of the components, such as the intercalary segment 118, is rotated with respect to the longitudinal axis of the femur. In some cases, the intercalary segment 118 is rotated (clockwise or counterclockwise) approximately one degree, five degrees, ten degrees, or other angles.

Referring to FIG. 2A, each of the intercalary segment 118 and modular body 100 may include one or more fastening apertures 120, for receiving the fasteners that couple the intercalary segment 118 and modular body 110. In one embodiment, each of the one or more apertures 120 are distributed on the intercalary segment 118 and modular body 110 such that the apertures 120 are generally horizontal. For example, screws can be inserted perpendicular to the axis of the stem 112 (i.e. perpendicular to the longitudinal axis of the femur), and into the modular body 110 or intercalary segment 118, and the stem 112.

Again referring to FIGS. 2 and 2A, according to one embodiment, a collar to couple to the modular body 110 and is configured to optimize the rotational alignment of the modular body 110 or intercalary segment 118 (see FIG. 2). For example, the collar includes notches at small angular intervals (e.g., 1 degree increments, 5 degree increments, or 10 degree increments, etc.). In another example, the collar can include an intercalary segment 118 of the megaprosthesis 100 that is configured to offset the rotation of the modular body 110 by an angular interval to couple the modular body 110 at a preferred (e.g., such as described below) or optimal alignment for the patient, as determined by the physician. In another example, the intercalary segment 118 or modular body 110 of the megaprosthesis 100 may be attached by way of a taper such as a male and female end coming together. A screw may be used to attach the modular body 110 or intercalary segment 118 to the stem 112. Thus, the rotational alignment of the megaprosthesis 100 and stem 112 can be optimized for each patient.

Referring to FIGS. 2-5, the stem 112 of the current embodiment is configured to be threadably attached, such as by screwing, to the patient's bone. The stem 112 has a cylindrical outer surface that includes threads 122 that extend from a proximal end 124 of the stem 112 to a distal end 126 of the stem 112. In one embodiment, the distal end 126 of the stem 112 is conic-like, such that the distal end 126 of the stem 112 is tapered. The stem 112 can be formed of many typical materials (e.g., titanium, stainless steel, cobalt chromium, or the like), with coatings as described below (e.g., hydroxyapatite, porous tantalum, elemental silver, or the like) and soft tissue attachment materials (e.g., polyester, polypropylene, carbon fiber, expanded polytetrafluoroethylene, or the like) to increase the likelihood of osteointegration. In some embodiments, the threads 122 may extend for only a portion of the length of the stem 112 such as only a quarter-, a third-, a half-length, or the like, of the stem 112 near the proximal end 124 of the stem 112.

In some embodiments, the stem 112 includes a surface that can be configured to encourage bone in-growth. In one embodiment, the surface of the stem 112, particularly the threads 122, has a hydroxyapatite coating to promote osteointegration. For example, the stem 112 of the megaprosthesis can be fixed to the patient's bone using an adhesive or cement, such as polymethymethacrylate (PMMA), or the like. The cement and megaprosthesis 100 could be further configured to be substantially spread between the threaded stem 112 and the interior surface of the bone when the threaded stem 112 is inserted into bone and harden when the threaded stem 112 is in a desired position. In one embodiment, the cement could be generally placed on an interior surface of the patient's bone, or alternatively, the cement could be generally placed on an outer surface of the stem 112. Thus, the cement can further fix the megaprosthesis 100 to the bone in a desired position when inserted into the bone.

In another embodiment, the surface of the stem is roughened (e.g., a scratch-like surface treatment). In another embodiment, at least a portion of the surface is relatively smooth compared to a typical roughened surface. In yet another embodiment, at least the collar and a portion of the stem 112 near the collar is roughened or coated to, for example, promote osteointegration and limit "stress shielding" compared to typical stems.

In one embodiment, the threads 122 of the stem 112 are configured to engage the bone (e.g., prepared or unprepared) to decrease the likelihood of subsidence, pull-out, or rotation. For example, the threads 122 may have an optimal particular thread pitch and height. In another embodiment, the thread pitch is variable between the proximal and distal portions of the stem 112. The stem 112 may have a tip at the distal end 126 that is tapered (like a screw rather than a bolt) for ease of insertion. The threads 122 of the stem 112 may be oriented for insertion of the stem in the canal of the bone in the clockwise or counterclockwise direction.

Again referring to FIGS. 2-5, the stem 112 is configured to fit various patients, such that the stem 112 has a length and diameter determined for each patient. For example, a manufacturer may choose to make stems 112 in lengths 5 cm, 8 cm, and 12 cm in diameters of 1 mm increments from 10 mm to 18 mm as to fit a spectrum of patients' anatomical needs. For example, patients with short remaining bone length may require stems 112 having shorter length. For example, patients with smaller diameter bone canals may require stems 112 of smaller diameter. For the shorter stems 112, having the entire stem 112 roughened would be likely ideal. In one embodiment, stems 112 that have a shorter length, such as less than 8 cm, have an outer surface that is completely roughened. In one embodiment, stems 112 that have a longer length, such as greater than 10 cm, may be only partially threaded, such that the portion near the proximal end 124 has threads 122 and roughened, and a portion near the distal end 126 of the stem 112 is smooth. The rationale for this would be that if the stem 112 needed to be removed in the future after osteointegration, it would not be difficult to remove the smooth portion of the stem 112 because that portion would be without bone ingrowth/ongrowth.

According to one embodiment, a method for inserting a modular megaprosthesis 100 includes using many typical techniques and tools used for inserting typical megaprosthesis replacements. The method includes determining the size (e.g., length and diameter) of the megaprosthesis 100, including the stem 112 and modular body 110, which is appropriate for the patient. In one embodiment, determining the size includes determining the stem 112 and modular body 110 based on the patient's local bone condition, including local revision history, bone density and strength, density, etc.

The method includes preparing the bone to securely fit the stem 112 and minimize preparation error. One embodiment of the method includes reaming the bone, such as by using typical orthopedic methods, to a length and diameter that is approximately the length and diameter of the stem 112. The lightness of the fit between the diameter of the stem 112 and the diameter of the prepared canal may be adjusted based on surgeon discretion and may depend on factors, such as the patient's bone quality, and the like. Thus, preparation the bone for a more secure fit between the bone and the threaded stem 112 to reduce the risk of loosening compared to typical megaprostheses. One embodiment of the method includes broaching of the bone in which instead of reaming and removal of the bone, the existing bone within the canal is impacted to the sides of the canal with a broach. One embodiment of the method includes no preparation of the bone prior to insertion of the stem 112. Yet another embodiment of the method includes drilling and tapping of the canal to form a path for the threads 122 on the stem 112, such as in the case of hard bone. One embodiment of the method further includes determining the desired rotational angular orientation of the modular body 110 or intercalary segment 118 with respect to the patient's native bone and implanted stem 112, for example. The rotational angular orientation of the modular body 110 or intercalary segment 118 with respect to the patient's native bone and implanted stem 112, for example. The rotational angular orientation of the intercalary segment 118 or modular body 110 may be based on anatomical landmarks, presurgical planning, intraoperative trialing and radiographic imaging.

The method further includes threading the stem 112 into the prepared bone. In one embodiment, threading the stem 112 into the prepared bone includes slowly rotating the stem 112 with sufficient hand pressure such that the threads 122 of the stem 112 engage the bone. In another embodiment, threading the stem 112 into the prepared bone includes using a tool that is configured to couple to a proximal end 124 of the stem 112 and rotate the stem 112 into the bone. For example, the tool may be similar to a wrench-like device. The method further includes coupling the modular body 110 to at least one of the collar (or in another embodiment, the intercalary segment 118) and stem 112. In one example, the method may further include coupling a separate collar to the stem 112.

In one embodiment of the invention, the method includes further securing of the stem 112 in a rotational angular alignment. For example, the method can include securing the stem 112 and megaprosthesis 100 by inserting one or multiple cross-pins 128 (see FIG. 2A) through the bone and stem 112. Inserting the cross-pins 128 includes locating apertures 130 in the stem 112 by determining the angular alignment of the stem 112, such as while threading the stem 112 into the prepared bone. The aperture 130 may have various angular alignment with respect to each other and to the collar or intercalary segment 118, however, the aperture 130 is generally radially-aligned and oriented perpendicular to the axis of the stem 112 and through the center axis of the stem 112. In other embodiments, locating the aperture 130 and their determining their alignment can also include using typical imaging techniques, such as ultrasound or X-ray, and the like. In another embodiment, locating the cross-pin apertures 130 and their determining their alignment including using a jig to help aim it through a small hole in the stem, for example, by coupling a proximal end of the jig to the stem 112 such that distal end of the jig aligns with the cross-pin apertures 130. Inserting cross-pins 128 through the bone and stem, according to another embodiment, further includes drilling through the bone and cross-pin apertures 130 and placing the cross-pins 128 in the cross-pin apertures 130, such as by screwing, impacting, or the like. Thus, the method further secures or "locks-in" the stem 112 and the megaprosthesis 100 to reduce likelihood of subsidence, rotation, and increases the hold of compression via the collar or intercalary segment 118 and the stem 112.

Figure 5:
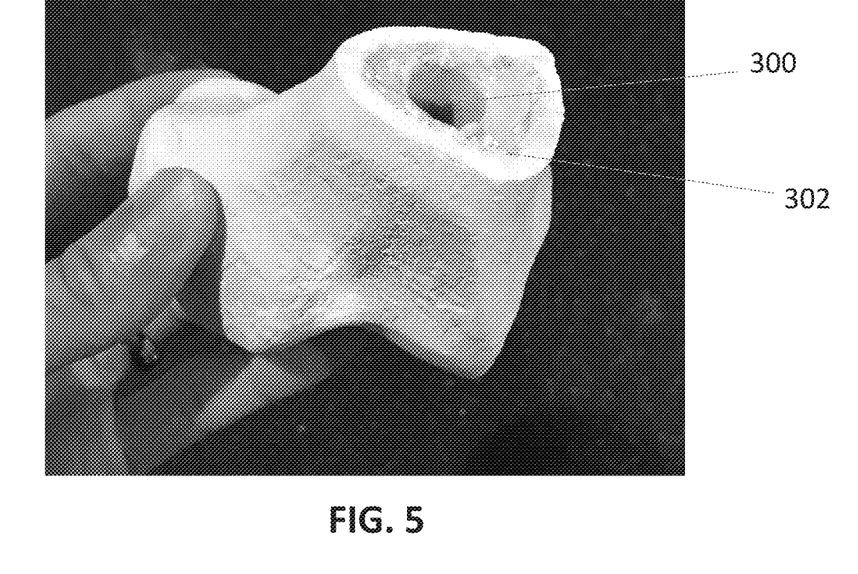
FIG. 5 is an image illustrating a short bone filled with cement and a path for the threaded stem.

In an embodiment, the method involves the use of the stem 112 for fixing with short bone. As used herein, "short bone" refers to a bone that lacks any remaining diaphysis. The short bone canal is first filled with cement. Referring to FIG. 6, a path 300 is created for the stem 112. The path 300 may be formed by filling cement around a smooth cylinder which is then removed, or by drilling after the cement has hardened. It is important that the diameter of the path 300 is slightly smaller than the diameter of the stem 112, preferably smaller than the outer diameter of the threads 122. Preferably, an introitus 302 free of cement is formed to allow for bone graft and additional surface for ingrowth. The stem 112 is then screwed into the path 300.

In certain embodiments, it may be necessary to remove the stem 112 from the bone, e.g. due to complication that arise after completion of the bone implant. In that case, a surgeon first removes any cross-pin(s) 128 holding the stem 112 in place, then backs the stem 112 out of the bone by unscrewing. If the stem is well-fixed, e.g. due to bone in-growth, the surgeon may disrupt the bone ingrowth using a chisel or other instruments before unscrewing the stem 112. Alternatively, it may be possible to resect the short segment of bone that contains the in-growth before unscrewing the stem 112. The unscrewing of the stem 112 allows for better control of the force required to remove the stem 112 compared to the prior art where tremendous force is used with a big slap-hammer to disimpact the prior art stem.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A megaprosthesis comprising
   a monolithic stem comprising
      an intercalary segment,
      a solid shaft configured to be inserted into a medullary canal, and
      a collar connecting the shaft to the intercalary segment,
      wherein the shaft comprises a tapered distal free end and a single cylindrical portion having a constant diameter to match an inner diameter of the medullary canal and locating between the free end and the collar,
      wherein the cylindrical portion comprises screw threads on a partial portion of its outer surface, while the remaining part of the outer surface comprises a roughened, knurled, porous, or hydroxyapatite coated surface with no screw thread,
      wherein the cylindrical portion comprises two apertures, each having a central axis perpendicular to and passing through a central axis of the cylindrical portion, the apertures extend about 90° to each other and are configured to receive cross-pins therein; and
   a modular body coupled to the intercalary segment by a male/female coupling, wherein the modular body is configured to replace at least the entire joint surface, the entire epiphysis, and the entire metaphysis of a bone.

2. The megaprosthesis of claim 1, wherein a portion of the shaft adjacent to the collar has a diameter larger than the diameter of the shaft in the location of the threads.

3. The megaprosthesis of claim 1, wherein the collar has a polygonal or circular perimeter.

4. The megaprosthesis of claim 1, wherein the modular body is an artificial joint or a bone replacement segment.

5. The megaprosthesis of claim 4, wherein the artificial joint is a replacement knee joint, hip joint, shoulder joint, wrist joint, ankle joint, elbow joint, joints of the hand, joints of the foot.

6. The megaprosthesis of claim 1, wherein the tapered distal free end of the shaft comprises a tapered point.

7. The megaprosthesis of claim 6, wherein the threads are located approximately midway between the taper point and the collar.

8. The megaprosthesis of claim 7, wherein the threads cover at least 50% of the shaft.

9. The megaprosthesis of claim 1, wherein the shaft further comprises a taper portion directly adjacent to the collar and locating between the collar and the cylindrical portion, the taper portion having no thread, tapers outwardly toward the diameter of the collar, and comprises a roughened, knurled, or porous surface.

10. The megaprosthesis of claim 9, wherein the threads cover at least 50% of the shaft.

11. The megaprosthesis of claim 1, wherein the modular body is fastened to the intercalary segment by a bolt, a screw, a pin, or a rivet.

12. The megaprosthesis of claim 1, wherein the outer surface of the stem comprises a hydroxyapatite coating.

13. The megaprosthesis of claim 1, wherein the threads cover at least 50% of the shaft.

14. The megaprosthesis of claim 1, wherein the collar is configured to mate with a tool to screw and advance the stem into a bone.

15. A method for implanting a megaprosthesis comprising the steps of
 a. providing the megaprosthesis of claim 1; and
 b. screwing the stem into the medullary canal.

16. The method of claim 15, further comprising the step of removing the entire joint surface, the entire epiphysis, and the entire metaphysis of a bone.

\* \* \* \* \*